(12) United States Patent
Hokenson et al.

(10) Patent No.: US 11,103,459 B2
(45) Date of Patent: *Aug. 31, 2021

(54) METHOD OF DRUG FORMULATION BASED ON INCREASING THE AFFINITY OF ACTIVE AGENTS FOR CRYSTALLINE MICROPARTICLE SURFACES

(71) Applicant: MannKind Corporation, Westlake Village, CA (US)

(72) Inventors: Mark Hokenson, Camarillo, CA (US); Keith A. Oberg, Valencia, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,736

(22) Filed: Oct. 4, 2018

(65) Prior Publication Data

US 2019/0029961 A1 Jan. 31, 2019

Related U.S. Application Data

(60) Division of application No. 15/233,794, filed on Aug. 10, 2016, now Pat. No. 10,143,655, which is a continuation of application No. 14/746,656, filed on Jun. 22, 2015, now Pat. No. 9,446,001, which is a division of application No. 12/883,369, filed on Sep. 16, 2010, now Pat. No. 9,089,497, which is a continuation of application No. 11/532,065, filed on Sep. 14, 2006, now Pat. No. 7,803,404.

(60) Provisional application No. 60/717,524, filed on Sep. 14, 2005, provisional application No. 60/744,882, filed on Apr. 14, 2006.

(51) Int. Cl.
| | |
|---|---|
| *A61K 38/13* | (2006.01) |
| *A61K 38/22* | (2006.01) |
| *A61K 38/25* | (2006.01) |
| *A61K 38/26* | (2006.01) |
| *A61K 38/27* | (2006.01) |
| *A61K 38/28* | (2006.01) |
| *A61K 38/29* | (2006.01) |
| *A61K 9/00* | (2006.01) |
| *A61K 9/16* | (2006.01) |
| *A61K 9/50* | (2006.01) |

(52) U.S. Cl.
CPC .......... *A61K 9/1676* (2013.01); *A61K 9/0073* (2013.01); *A61K 9/167* (2013.01); *A61K 9/1611* (2013.01); *A61K 9/1617* (2013.01); *A61K 9/1623* (2013.01); *A61K 9/5052* (2013.01); *A61K 9/5089* (2013.01); *A61K 38/13* (2013.01); *A61K 38/22* (2013.01); *A61K 38/25* (2013.01); *A61K 38/26* (2013.01); *A61K 38/27* (2013.01); *A61K 38/28* (2013.01); *A61K 38/29* (2013.01)

(58) Field of Classification Search
CPC ........ A61K 38/13; A61K 38/22; A61K 38/25; A61K 38/26; A61K 38/27; A61K 38/28; A61K 38/29; A61K 9/0073; A61K 9/1611; A61K 9/1617; A61K 9/1623; A61K 9/167; A61K 9/1676; A61K 9/5052; A61K 9/5089
USPC ................. 514/11.3, 11.8, 5.9, 9.7; 424/491
See application file for complete search history.

(56) References Cited

U.S. PATENT DOCUMENTS

| | | | |
|---|---|---|---|
| 5,503,852 A * | 4/1996 | Steiner ................. | A61K 9/1617 424/489 |
| 6,444,226 B1 * | 9/2002 | Steiner ................. | C07K 14/605 424/489 |
| 2006/0260777 A1 * | 11/2006 | Rashba-Step ........ | A61K 9/5057 162/181.1 |

* cited by examiner

*Primary Examiner* — Julie Ha
(74) *Attorney, Agent, or Firm* — Withers Bergman LLP; Alan D. Gardner

(57) ABSTRACT

Methods are provided for promoting the adsorption of an active agent to microparticles by modifying the structural properties of the active agent in order to facilitate favorable association to the microparticle.

15 Claims, 11 Drawing Sheets

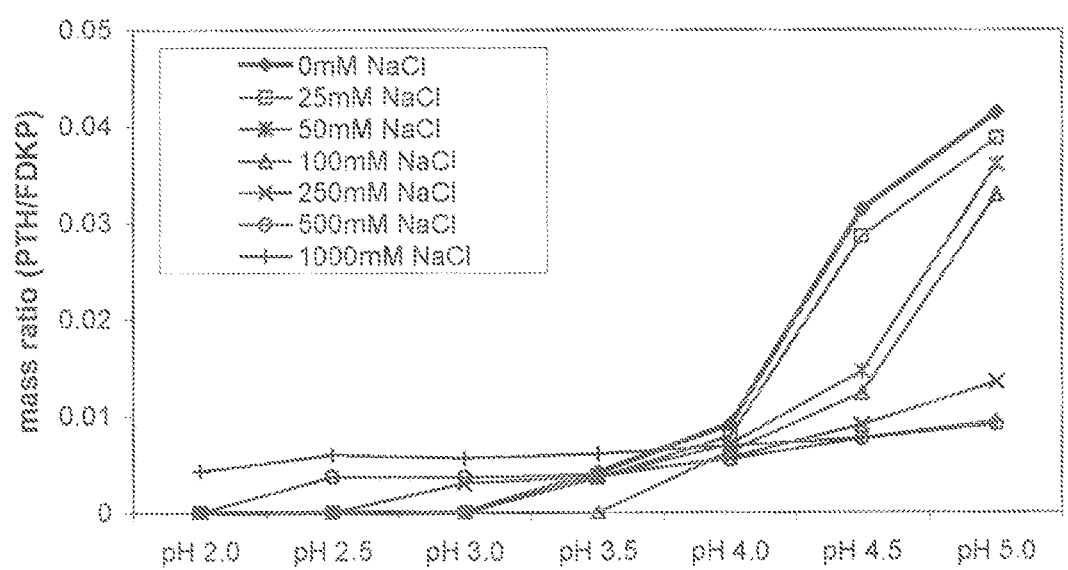

FIG. 5B

Figure 1A:
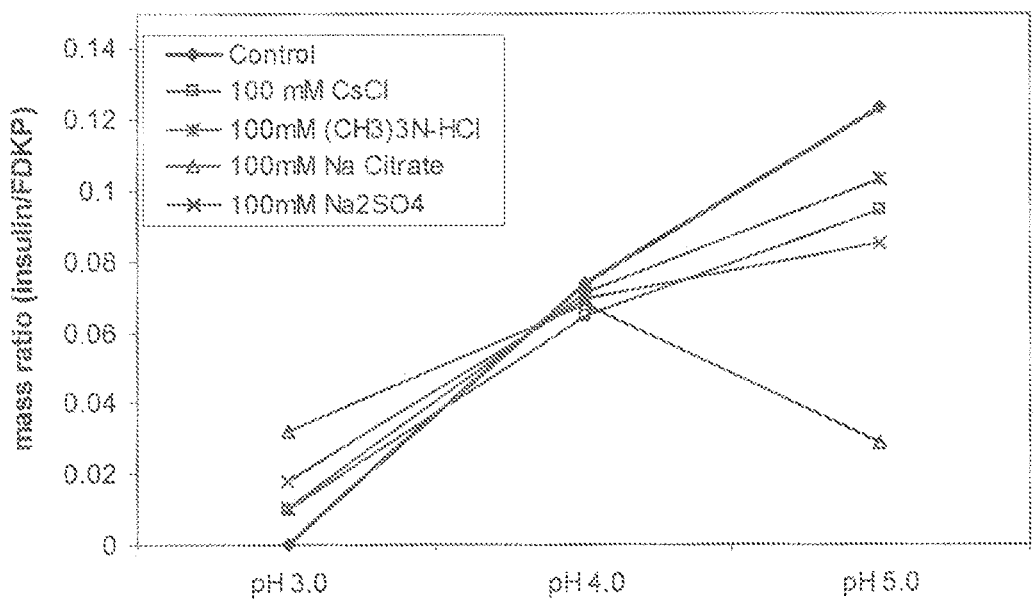

METHOD OF DRUG FORMULATION BASED ON INCREASING THE AFFINITY OF ACTIVE AGENTS FOR CRYSTALLINE MICROPARTICLE SURFACES

CROSS REFERENCE TO RELATED APPLICATIONS

The present application is a divisional of U.S. patent application Ser. No. 15/233,794, filed Aug. 10, 2016, which is a continuation of U.S. patent application Ser. No. 14/746,656 filed Jun. 22, 2015, which is a divisional of U.S. patent application Ser. No. 12/883,369 filed Sep. 16, 2010, which is a continuation of U.S. patent application Ser. No. 11/532,065 filed Sep. 14, 2006 and claims the benefit under 35 U.S.C. § 119(e) to U.S. Provisional Application Ser. No. 60/717,524 filed on Sep. 14, 2005, and 60/744,882, filed on Apr. 14, 2006, the entire contents of each which are hereby incorporated by reference in their entirety.

FIELD OF THE INVENTION

This invention relates to drug formulations and is particularly related to methods. More specifically, binding or adsorbing active agents onto the surface of crystalline microparticles is disclosed.

BACKGROUND OF THE INVENTION

Delivery of therapeutic agents has been a major problem. Oral administration is one of the most common and preferred routes of delivery due to ease of administration, patient compliance, and decreased cost. However, the disadvantages of this route include low or variable potency and inefficient adsorption of the therapeutic. This is particularly evident when the compound to be delivered is unstable under conditions encountered in the gastrointestinal tract. A variety of coatings and encapsulation methods have been developed in the art, but only a few are effective in addressing this issue. Still, there are therapeutic compounds that tend to be less active in the conditions of the gastrointestinal tract and must be administered in higher dosages to be adsorbed into the bloodstream in an effective amount.

A broad range of drug formulation systems have been developed to address the problem of optimal drug delivery and are based on incorporation of drug into a matrix that acts as a carrier. Factors considered in drug formulation include requirements that the system be non-toxic and non-reactive with the drug to be delivered, economical to manufacture, formed of readily available components, and consistent with respect to final composition and physical characteristics, including stability and release rate. It is also preferable that the drug delivery system is formed of materials easily removed from the body by normal physiologic processes.

Advancements in microparticle technology have aided in the development of improved drug formulations. However, despite these advances there is still a need in the art for stable drug formulations having long term effectiveness and optimal adsorption when administered as a pharmaceutical, particularly by pulmonary means. One approach in addressing this deficiency is to target the structural characteristics/properties of the active agent that would promote its adsorption to the microparticle surface and decrease its tendency to remain in solution.

SUMMARY OF THE INVENTION

Methods are provided for binding, coating or adsorbing an active agent onto a crystalline microparticle surface. In general, microparticles are coated with an active agent by modifying the system comprising the microparticles and the dissolved active agent such that the active agent has a greater affinity for the microparticle surface than for remaining in solution. In particular the present invention seeks to further promote the adsorption of an active agent to the microparticle surface by modifying/utilizing the properties of the active agent under a number of conditions in solution.

Thus, in the present invention there is provided a method for promoting binding of an active agent to a preformed crystalline microparticle in suspension comprising the steps of: i) modifying the chemical potential of the active agent wherein the modifying allows for an energetically favorable interaction between the active agent and microparticle independent of removal of solvent; and ii) adsorbing the active agent onto the surface of the microparticle.

In particular embodiments of the present invention, modifying the chemical potential comprises modifying the structure, flexibility, rigidity, solubility or stability of the active agent, individually or in combination. Modifying the chemical potential of the active agent comprises altering solution conditions. Altering solution conditions comprises adding an active agent modifier to the solution.

In particular embodiments, the active agent modifier is selected from the group consisting of salts, surfactants, ions, osmolytes, alcohols, chaotropes, kosmotropes, acids, bases, and organic solvents. In one embodiment, the salt is sodium chloride.

In still yet another embodiment of the present invention, the method further comprises the step of dissolving the active agent in the fluid phase of a suspension of microparticles and changing the pH of the fluid phase. In one aspect the step of dissolving the active agent in a fluid phase refers to the dissolving of a solid. In another aspect the step of dissolving the active agent refers to the addition of a concentrated solution of the active agent.

In another embodiment of the present invention, the active agent modifier improves the structural stability of the active agent.

In yet another embodiment of the present invention the active agent is a protein, peptide, polypeptide, small molecule, or nucleic acid molecule. In another embodiment of the present invention the active agent is selected from the group consisting of insulin, ghrelin, growth hormone, and parathyroid hormone (PTH). The active agent can comprise an antibody or antibody fragment. In various aspects of the invention the antibody can recognize a disease-associated antigen including, without limitation, a tumor-associated antigen or an infectious pathogen-related antigen.

In still yet another embodiment of the present invention, the small molecule is an ionizable molecule or a hydrophobic molecule such as, but not limited to, cyclosporin A.

In another embodiment of the present invention, modifying the chemical potential of the active agent comprises modulating one or more energetically favorable interactions such as, but not limited to, electrostatic interactions, hydrophobic interactions, and/or hydrogen bonding interactions between the active agent and the microparticle surface. In one embodiment, the microparticle comprises a diketopiperazine such as, but not limited to, fumaryl diketopiperazine.

In yet another embodiment of the present invention, the method further comprises a step for removing or exchanging the solvent. Solvent, as used herein, refers to the fluid medium in which the active agent and microparticle are "bathed." It should not be interpreted to require that all components are in solution. Indeed in many instances it may be used to refer to the liquid medium in which the microparticles are suspended.

In another embodiment of the present invention, there is provided a process for preparing a drug delivery composition comprising an active agent and a crystalline microparticle comprising the steps of: providing an active agent solution comprising an active agent molecule; modifying the chemical potential of the active agent; providing a microparticle in a suspension or powder; and combining the active agent solution with the microparticle suspension or powder. The powder can be, for example, filtered but not dried.

In another embodiment of the present invention, the process of modifying the chemical potential of the active agent allows for interaction between the active agent and a microparticle. In one embodiment, modifying the chemical potential of the active agent comprises adding an active agent modifier to the solution. Such an active agent modifier can be selected from the group consisting of salts, surfactants, ions, osmolytes, alcohols, chaotropes, kosmotropes, acid, base, and organic solvents. In yet another embodiment, the modifier decreases the solubility of the active agent molecule, promotes association between the active agent and a microparticle such as a diketopiperazine particle, and/or improves the structural stability of the active agent molecule.

BRIEF DESCRIPTION OF THE DRAWINGS

The following drawings form part of the present specification and are included to further demonstrate certain aspects of the examples disclosed herein. The invention may be better understood by reference to one or more of these drawings in combination with the detailed description of specific embodiments presented herein.

FIGS. 1A-1C depict the effects of chaotropes and kosmotropes on loading curves for active agents onto fumaryl diketopiperazine (FDKP) microparticles as a function of pH and 100 mM chaotropic/kosmotropic agent according to the teachings of the present invention. FIG. 1A depicts the loading of 0.75 mg/mL insulin onto 5 mg/mL FDKP microparticles in the presence of chaotropes and kosmotropes at pH 3.0-5.0. FIG. 1B depicts the loading of 0.25 mg/mL glucagon-like peptide 1 (GLP-1) onto 5 mg/mL FDKP microparticles in the presence of chaotropes and kosmotropes at pH 2.0-4.0. FIG. 1C depicts the loading of 0.25 mg/mL parathyroid hormone (PTH) onto 5 mg/mL FDKP microparticles in the presence of the strong chaotropes, NaSCN and $NaClO_4$, between pH 4.0-5.0.

FIGS. 2A-2C depict the effects of osmolytes on loading curves for active agents onto FDKP microparticles as a function of pH and osmolytes (100 mM) according to the teachings of the present invention. FIG. 2A depicts the loading of 0.75 mg/mL insulin onto 5 mg/mL FDKP microparticles in the presence of osmolytes at pH 3.0-5.0. FIG. 2B depicts the loading of 0.25 mg/mL GLP-1 onto 5 mg/mL FDKP microparticles in the presence of osmolytes between pH 2.0-4.0. FIG. 2C depicts the loading of 0.10 mg/mL ghrelin peptide onto 5 mg/mL FDKP microparticles in the presence of strong osmolytes at pH 4.0-5.0.

FIGS. 3A-3D depict the effects of alcohols on loading curves for active agents onto FDKP microparticles as a function of pH and alcohols according to the teachings of the present invention. FIG. 3A depicts the loading of 0.10 mg/mL ghrelin onto 5 mg/mL FDKP microparticles in the presence of hexafluoroisopropanol (HFIP) at 5%, 10%, 15%, and 20% v/v between pH 2.0-4.0. FIG. 3B depicts the loading of 0.10 mg/mL ghrelin onto 5 mg/mL FDKP microparticles in the presence of trifluoroethanol (TFE) at 5%, 10%, 15%, and 20% v/v between pH 2.0-4.0. FIGS. 3C and 3D depict the loading of 0.25 mg/mL GLP-1 onto 5 mg/mL FDKP microparticles at pH 2.0-5.0 in the presence of HFIP and TFE, respectively.

FIGS. 4A-4D depict the effects of salt on loading curves for active agents onto FDKP microparticles as a function of pH and NaCl concentration according to the teachings of the present invention. FIG. 4A depicts the loading of 0.75 mg/mL insulin onto 5 mg/mL FDKP microparticles in the presence of 0-500 mM NaCl at pH 2.0-5.0. FIG. 4B depicts the loading of 0.25 mg/mL GLP-1 onto 5 mg/mL FDKP microparticles in the presence of 0-500 mM NaCl at pH 2.0-5.0. FIG. 4C depicts the loading of 0.25 mg/mL PTH peptide onto 5 mg/mL FDKP microparticles in the presence of 0-1000 mM NaCl at pH 2.0-5.0. FIG. 4D depicts the secondary structural analysis of PTH at various salt concentrations (20° C.). The far-UV CD of 4.3 mg/mL PTH at pH 5.8 illustrates that as the concentration of NaCl increases the secondary structure of the peptide adopts a more helical conformation.

FIGS. 5A-5B depict the adsorption of hydrophobic molecules onto microparticles according to the teachings of the present invention. FIG. 5A depicts the binding of cyclosporin A to FDKP microparticles with increasing anti-solvent (water) at 60%, 80% and 90% concentration. FIG. 5B depicts the percent of theoretical maximum load achieved for cyclosporin A at varying mass ratios of cyclosporin A/FDKP microparticles in the presence of 90% anti-solvent.

FIG. 6 depicts the pharmacokinetics of single intravenous injection (IV) and pulmonary insufflation (IS) in rats using various mass ratios of cyclosporin A/FDKP microparticles at 90% anti-solvent according to the teachings of the present invention.

DETAILED DESCRIPTION OF THE INVENTION

Described herein are methods useful for stabilizing pharmaceutical active agents in combination with crystalline microparticles. The resulting compositions provide stable active agents coated onto the crystalline microparticle surfaces.

The substance to be coated or adsorbed onto the crystalline microparticle is referred to herein as active agent. Examples of classes of active agent include pharmaceutical compositions, synthetic compounds, and organic macromolecules that have therapeutic, prophylactic, and/or diagnostic utility.

Generally, most active agents can be coated or adsorbed onto the surface of crystalline microparticles including, but not limited to, organic macromolecules, nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 30 amino acid residues but may include more. Proteins are polymers that can contain more than 30 amino acid residues. The term polypeptide as is know in the art and as used herein, can refer to a peptide, a protein, or any other chain of amino acids of any length containing multiple peptide bonds, though generally containing at least 10 amino acids. The active agents used in the coating formulation can fall under a variety of biological activity classes, such as vasoactive agents, neuroactive agents, hormones, anticoagulants, immunomodulating agents, cytotoxic agents, antibiotics, antivirals, antigens, and antibodies.

Examples of active agents that may be employed in the present invention include, in a non-limiting manner: growth hormone, antibodies and fragments thereof, alkynes, cyclosporins (e.g. cyclosporin A), PPACK (D-phenylalanyl-L-prolyl-L-arginine chloromethyl ketone), CMFDA (5-chloromethylfluorescein diacetate), Texas Red, clopiogrel, granulocyte macrophage colony stimulating factor (GM-CSF), glucagon-like peptide 1 (GLP-1), ghrelin, parathyroid hormone (PTH), insulin and insulin analogs (e.g., aspart insulin and insulin), and antibodies and fragments thereof, including, but not limited to: humanized or chimeric antibodies; F(ab), F(ab)2, or single-chain antibody alone or fused to other polypeptides; therapeutic or diagnostic monoclonal antibodies to cancer antigens, cytokines, infectious agents, inflammatory mediators, hormones, and cell surface antigens. Non-limiting examples of antibodies to tumor antigens include anti-SSX-241-49 (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen), anti-tyrosinase (melanoma tumor associated antigen), and anti-MOPC-21 (myeloma plasma-cell protein).

Microparticles

Essentially, the term "microparticle" refers to a particle with a diameter of about 0.5-1000 @m, irrespective of the precise exterior or interior structure. Within the broad category of microparticles, "microspheres" refers to microparticles with uniform spherical shape. Crystalline microparticles as used herein refers to microparticles that have the internal structure, though not necessarily the external form, of a crystal and have a regular arrangement of atoms in a space lattice. Ionizable crystalline surfaces refer to crystalline microparticles that have the additional capacity to carry an electrical charge. In some embodiments the microparticle can be a single regularly shaped crystal. In various preferred embodiments the microparticle is irregularly shaped, is porous, has dissolved active agent-accessible interior surfaces, or comprises multiple crystals, in any combination. Such characteristics will generally increase surface area and thereby loading capacity. Such characteristics can also contribute to advantageous aerodynamic properties, important if the active agent is to be delivered by inhalation of a dry powder comprising the microparticles.

Preferably, the chemical substance composing the crystalline microparticle is reversibly reactive with the active agent to be delivered, non-toxic, as well as non-metabolized by rodents and humans. The foregoing notwithstanding, some levels of toxicity are tolerable, depending, for example, on the severity of the condition to be treated or the amount of the substance to which a patient is exposed. Similarly, it is not required that the substance be completely metabolically inert. In addition, the crystalline structure of preferred microparticles is not substantially disrupted in the process of coating or binding with active agent. The composition of the crystalline microparticle determines what type of chemical interactions can be manipulated to drive adsorption of an active agent to the microparticle surface.

A number of substances can be used to form crystalline microparticles. Microparticles as such have surfaces, the properties of which can be manipulated in the coating process as disclosed in copending U.S. patent application Ser. No. 11/532,063, filed on the same date as the instant application, and U.S. Provisional Application Ser. No. 60/717,524 filed on Sep. 14, 2005, each of which is hereby incorporated by reference in its entirety. Representative materials from which crystalline microparticles can be formed include, but are not limited to, aromatic amino acids, or compounds with limited solubility in a defined pH range such as diketopiperazines and morpholine sulfates.

One particular example of microparticles as contemplated in the present invention are diketopiperazine (DKP) microparticles. As discussed herein, DKP microparticles are employed to facilitate the adsorption of the active agent. U.S. Pat. Nos. 5,352,461 and 5,503,852, each of which is incorporated herein by reference in its entirety, describe a drug delivery system based on formation of diketopiperazine (DKP) microparticles from diketopiperazine derivatives such as 3,6-bis[N-fumaryl-N-(n-butyl)amino] (also referred to as fumaryl diketopiperazine or FDKP; also termed (E)-3,6-bis[4-(N-carboxy-2-propenyl)amidobutyl]-2,5-diketopiperazine) that are stable at low pH and dissolve at the pH of blood or the small intestine. A system based on diketopiperazine structural elements or one of its substitution derivatives, including, but not limited to, diketomorpholines and diketodioxanes, forms microparticles with desirable size distributions and pH ranges as well as good payload tolerance. A wide range of stable, reproducible characteristics can be generated with appropriate manipulations of the substituent groups. These patents disclosed precipitation of the DKP in the presence of the active agent to form microparticles comprising the active agent. Further details for synthesis, preparation, and use of diketopiperazines and diketopiperazine microparticles are disclosed in U.S. Pat. Nos. 6,071,497; 6,331,318; 6,428,771 and U.S. Patent Publication Nos. 20060040953 and 20060041133, each incorporated herein by reference in their entirety. Compositions comprising diketopiperazine particles are disclosed in U.S. Pat. No. 6,991,779 and U.S. Patent Publication No. 20040038865; each incorporated herein by reference in their entirety.

Other diketopiperazines contemplated in the present invention include 3,6-di(4-aminobutyl)-2,5-diketopiperazine; 3,6-di(succinyl-4-aminobutyl)-2,5-diketopiperazine (succinyl diketopiperazine or SDKP); 3,6-di(maleyl-4-aminobutyl)-2,5-diketopiperazine; 3,6-di(citraconyl-4-aminobutyl)-2-5-diketopiperazine; 3,6-di(glutaryl-4-aminobutyl)-2,5-diketopiperazine; 3,6-di(malonyl-4-aminobutyl)-2,5-diketopiperazine; 3,6-di(oxalyl-4-aminobutyl)-2,5-diketopiperazine and derivatives therefrom. Diketopiperazine salts may also be utilized in the present invention and may included, for example, a pharmaceutically acceptable salt such as the Na, K, Li, Mg, Ca, ammonium, or mono-, di- or tri-alkylammonium (as derived from triethylamine, butylamine, diethanolamine, triethanolamine, or pyridines, and the like). The salt may be a mono-, di-, or mixed salt. Higher order salts are also contemplated for diketopiperazines in which the R groups contain more than one acid group. In other aspects of the invention, a basic form of the agent may be mixed with the diketopiperazine in order to form a salt linkage between the drug and the diketopiperazine, such that the drug is a counter cation of the diketopiperazine. DKP salts for drug delivery are disclosed in a further detail in U.S. Patent Application Publication No. 20060040953 which is herein incorporated by reference in its entirety.

U.S. Pat. Nos. 6,444,226, and 6,652,885, each herein incorporated by reference in their entirety, describe preparing and providing microparticles of DKP in aqueous suspension to which a solution of active agent is added, and then the critical step of lyophilizing the suspension to yield microparticles having a coating of active agent. The basis for this formulation is that the coating of microparticle with active agent is driven by removal of the liquid medium by lyophilization. (See also U.S. Pat. No. 6,440,463 which is incorporated herein by reference in its entirety). In contrast to teachings in the prior art, the present invention provides means for adjusting the association of active agent with the microparticle prior to solvent removal. Thus, removal of the liquid medium by bulk physical methods (e.g., filtration or sedimentation) or evaporative methods (e.g., lyophilization or spray-drying) can result in comparable loads.

Promoting Adsorption of Active Agents

Adsorbing active agent to the surface of a crystalline microparticle can involve altering the properties of the active agent in a solution or fluid suspension under various solution conditions, thereby promoting adsorption to the microparticle surface and reducing the amount of active agent remaining in solution. Alteration or modifications to the active agent may occur with the use of modifiers such as, but not limited to, chaotropes and kosmotropes, salts, organics such as, but not limited to, alcohols, osmolytes, and surfactants. These modifiers can act on the active agent to alter its chemical potential and thereby its structure, flexibility, rigidity or stability, without chemically altering the agent itself. The term "chemical potential" is well known to one of ordinary skill. In embodiments of the present invention, "chemical potential" refers to the free energy necessary to drive a chemical reaction such as, for example, interaction between an active agent and a solvent or the adsorption of active agent onto a microparticle. The term "energetically favorable" as used herein refers to the lowering of the free energy levels of the absorbed states of the active agent onto the microparticle in relation to the free energy level of uncoated microparticle, or unbound active agent and/or the insoluble forms (including aggregation or precipation) of the active agent. The term "structure" as used herein refers to the secondary structure of the active agent molecule and includes the alpha-helical formation, beta sheets, or random coil (unordered) of the active agent molecule, such as a protein. Additionally, the term structure may also include teritary and quaternary structures of the molecule but is not limited to such and may also refer to the self association, aggregation, multimerization, dimerization, and the like, of a molecule. The term "stability" as used herein refers to the stabilization or destabilization of the structure of the active agent in the presence of the modifier.

In addition, altering the properties of the active agent in a solution or fluid suspension are likely to affect the interactions due to hydrophobic properties, hydrogen bonding properties, and electrostatic properties of the active agent and/or microparticle.

Hydrophobic interactions are associations of non-polar groups with each other in aqueous solutions because of their insolubility in water. Hydrophobic interactions can affect a number of molecular processes including, but not limited to, structure stabilization (of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (typically an F, O, or N atom on another molecule). Hydrogen bonds are responsible for the unique properties of water and are very important in the organization of biological molecules, especially in influencing the structure of proteins and DNA.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Electrostatic interactions are also of importance when considering interaction and adhesion between particles.

Salts

In some embodiments of the present invention, the properties of the active agent are altered using a salt such as, but not limited to, sodium chloride. Active agents, for example, PTH and GLP-1, undergo noticeable structural changes in the presence of salt. As shown in Example 5 (FIG. 4D), the presence of salt increases the secondary structure of PTH by promoting a more helical conformation of the peptide. Salt has also been shown to affect the structure of GLP-1, as disclosed in U.S. Provisional Patent Application, Ser. No. 60/744,882, filed on Apr. 14, 2006 and incorporated herein by reference in its entirety. Furthermore, salts and other ionic compounds are capable of either stabilizing or destabilizing proteins and peptides, especially when the difference between the pH of the solution and the pI of the protein or peptide becomes greater, by binding to specifically charged residues (Antosiewiez J, et al., *J. Mol. Biol.* 238:415-436, 1994).

Chaotropes

Chaotropes, as are well known in the art, are ions that exhibit weak interactions with water and therefore destabilize molecules such as proteins or peptides. These compounds break down the hydrogen-bonded network of water and decrease its surface tension, thus promoting more structural freedom and denaturation of proteins and peptides. Examples of chaotropes include, but are not limited to, NaSCN, $(CH_3)_3N$—HCl, $Na_2NO_3$, and $NaClO_4$ and cesium chloride (CsCl).

Kosmotropes or lyotropes, on the other hand, are ions that display strong interactions with water and generally stabilize macromolecules such as proteins and peptides. This stabilization effect is brought about by increasing the order of water and increasing its surface tension. Examples of kosmotropes include, but are not limited to, sodium citrate (Na Citrate), and sodium sulfate ($Na_2SO_4$).

Alcohols

Another class of modifier of active agent employed in the present invention is alcohols. Alcohols are able to disrupt the native structure of proteins and peptides and are also able to stabilize and induce @-helical conformations in macromolecules, most notably within unstructured proteins and polypeptides. Such alcohols may include, but are not limited to, methanol (MeOH), ethanol (EtOH), trifluoroethanol (TFE), and hexafluoroisopropanol (HFIP). Of those, TFE and HFIP are two of the most potent alcohols for inducing helical transitions in peptides and proteins (Hirota et al., *Protein Sci.,* 6:416-421; 1997, incorporated herein by reference for all it contains regarding helical transitions in peptides and proteins). These alcohols may affect the structure of proteins and peptides through their ability to disrupt the hydrogen-bonding properties of the solvent (see Eggers and Valentine,

*Protein Sci.*, 10:250-261; 2001, incorporated herein by reference for all it contains regarding the effect of alcohols on the structure of proteins).

Osmolytes

Another class of modifier that affects the active agent affinity for the microparticle is osmolytes. Osmolytes, as are well known to the skilled artisan, are small compounds that are produced by the cells of most organisms in high stress situations (such as extreme temperature fluctuations, high salt environments, etc.) to stabilize their macromolecules. They do not interact with the macromolecule directly but act by altering the solvent properties in the cellular environment and so their presence indirectly modifies the stability of proteins. These compounds include various polyols, sugars, polysaccharides, organic solvents, and various amino acids and their derivatives. Although the mechanism of osmolytes are yet to be elucidated, it is speculated that these compounds likely act by raising the chemical potential of the denatured state relative to the native state, thereby increasing the (positive) Gibbs energy difference ($\Delta G$) between the native and denatured ensembles (Arakawa and Timasheff, *Biochemistry* 29:1914-1923; 1990).

Osmolytes as contemplated in the present invention, include in a non-limiting manner, hexylene-glycol (Hex-Gly), trehalose, glycine, polyethylene glycol (PEG), trimethylamine N-oxide (TMAO), mannitol, and proline.

General Description of the Method

In the methods of the present invention, at least three components are combined in a liquid medium: at least one active agent, (preformed) microparticles, and at least one active agent modifier as described above. The components of this system may be combined in any order. In some embodiments the modifier and active agent are combined with each other prior to that mixture being combined with a suspension of microparticles. In other embodiments the agent and microparticles are first combined and then the modifier is added. In some embodiments the active agent or modifier is provided and combined with another component, or components, as a solution. In other embodiments any of the components can be provided in solid form and dissolved, or in the case of the microparticles, suspended, in the liquid medium containing another of the components. Further variations will be apparent to one of skill in the art.

The microparticles are formed prior to being combined with the other components of the system, and as such are present as a suspension. Nonetheless the liquid medium in which the microparticles are suspended is at times referred to herein as a solvent. The liquid medium utilized in the method is most often aqueous. However in some instances the liquid medium can comprise more of an organic compound, for example an alcohol used as a modifier, than it does water.

Upon assembly of all components of the system, the active agent will adsorb to the surface of the microparticle. In increasingly preferred embodiments of the present invention, at least 50, 60, 70, 80, 90, 95%, or substantially all, of the active agent in the system will adsorb to the microparticles, up to 100%. In some embodiments of the present invention, the accessible surface area of the microparticles with be sufficient for all of the adsorbed active agent to be in direct contact with the microparticle surface, that is, the coating is a monolayer. However it is to be understood that additional interactions can be present. In some instances, for example, self-association of the active agent can also be energetically favored so that multiple layers of active agent coat the particle. It is not required that any of these layers be complete or that the thickness of the coating be uniform.

Two forms of self-association can be recognized: multimerization and aggregation. Multimerization is characterized by specific intermolecular interactions and fixed stoichiometry. Aggregation is characterized by unspecific intermolecular interactions and undefined stoichiometry. It should be understood that multimeric active agents can be adsorbed in the multimeric state, or dissociated into monomers, or lower order multimers, and adsorbed to the surface in that state. In either case aggregation can mediate layering of the active agent onto the microparticle.

The loaded microparticles constitute a drug delivery composition that can be utilized in a variety of forms. The particles can be used as powders, in solid dosage forms such as tablets or contained in capsules, or suspended in a liquid carrier. Generally this will require exchange and/or removal of the liquid medium in which the loading took place. This can be accomplished by any of a variety of means including physical methods such as, but not limited to, sedimentation or filtration, and evaporative methods such as, but not limited to, lyophilization or spray-drying. These techniques are known to those skilled in the art. In one embodiment of the present invention, solvent is removed by spray-drying. Methods of spray-drying diketopiperazine microparticles are disclosed in, for example, U.S. Provisional Patent Application No. 60/776,605 filed on Feb. 22, 2006, incorporated by reference herein for all it contains regarding spray-drying diketopiperazine microparticles.

If loading is not substantially complete, embodiments of the invention, using physical methods of solvent removal will typically loose the unadsorbed active agent, but for example can be useful to ensure that coating does not progress beyond a monolayer. Conversely, embodiments using evaporative drying for solvent removal can in some cases deposit additional active agent on the particle and thereby avoid its loss, but the adsorptive interactions involved can differ from those established by the molecules bound in the earlier steps of the method. In other embodiments evaporative solvent removal does not result in significant further deposition of active agent, including the case in which substantially all of the active agent was already adsorbed to the particle.

EXAMPLES

The following examples are included to demonstrate preferred embodiments of the present invention. It should be appreciated by those of skill in the art that the techniques disclosed in the examples which follow represent techniques discovered by the inventor to function well in the practice of the invention, and thus can be considered to constitute preferred modes for its practice. While discussion may focus on a particular mechanism it should be understood that some modifiers can have multiple effect on the agent, or indeed on the particle surface as well, each of which can contribute to promoting adsorption of the agent to the particle. However, those of skill in the art, in light of the present disclosure, will appreciate that many changes can be made in the specific embodiments which are disclosed and still obtain a like or similar result without departing from the spirit and scope of the invention.

Example 1

Experimental Procedure: Active Agent/FDKP Microparticle Adsorption Studies

The active agents insulin, PTH, ghrelin and GLP-1 were either purchased from American Peptide (Sunnyvale, Calif.)

or AnaSpec (San Jose, Calif.), or prepared in house (MannKind Corporation, Valencia, Calif.). Aqueous samples at varying pH and at 20° C. (unless otherwise noted) were analyzed. Samples were generally prepared fresh and were mixed with the particular additive (e.g., salt, pH buffer, etc., if any), prior to the addition of FDKP microparticles.

The association of active agent with diketopiperazine (DKP) particles in suspension was evaluated by conducting adsorption studies. The parameters investigated in the adsorption studies explored the effects of electrostatic interactions, hydrogen bonding, water structure, protein flexibility, and specific salt-pairing interactions on the active agent/ fumaryl diketopiperazine (FDKP) microparticle interaction. In addition, several common protein stabilizers were tested for interference with active agent adsorption to FDKP microparticle surfaces.

Varying conditions promoting adsorption of active agent onto the surfaces of preformed FDKP particles were studied. A 15 mg/mL FDKP microparticle suspension was combined with 3×pH buffer and 3× solution of an additive or excipient. The final solution contained a FDKP microparticle concentration of 5 mg/mL and a GLP-1 concentration of 0.25 mg/mL (5% w/w), or a PTH concentration of 0.25 mg/mL (5% w/w), or an insulin concentration of 0.75 mg/mL (15% w/w) or a ghrelin concentration of 0.10 mg/mL (2% w/w). Unbound active agent in the supernatant was filtered off the suspension. The FDKP particles with the associated active agent were dissolved (reconstituted) in 100 mM ammonium bicarbonate and filtered to separate out any aggregated active agent molecules. The amount of active agent in both the supernatant and reconstituted fractions was quantitated by HPLC. A series of experiments were conducted in which conditions employed included use of additives such as salts, osmolytes, chaotropes and kosmotropes, and alcohols. The results from these studies are described below.

Example 2

Effect of Chaotropes and Kosmotropes on Adsorption of Active Agent onto FDKP Particles Ionic species that affect the structure of water and proteins (chaotropes and kosmotropes) were studied to investigate the adsorption of active agent onto a FDKP microparticle surface by a hydrophobic mechanism (at low pH). Loading of the active agent onto FDKP particles was performed at 5 mg/mL microparticles and a GLP-1 concentration of 0.25 mg/mL (5% w/w), or a PTH concentration of 0.25 mg/mL (5% w/w), or an insulin concentration of 0.75 mg/mL (15% w/w). The concentration of the chaotrope or kosmotrope in the samples was held constant at 100 mM and the pH varied from 2.0 to 5.0. Chaotropes or kosmotropes were selected from the following: NaSCN, CsCl, $Na_2SO_4$, $(CH_3)_3N$—HCl, $Na_2NO_3$, Na Citrate, and $NaClO_4$. The control indicates no chaotrope or kosmotrope were added.

Figure 1B:
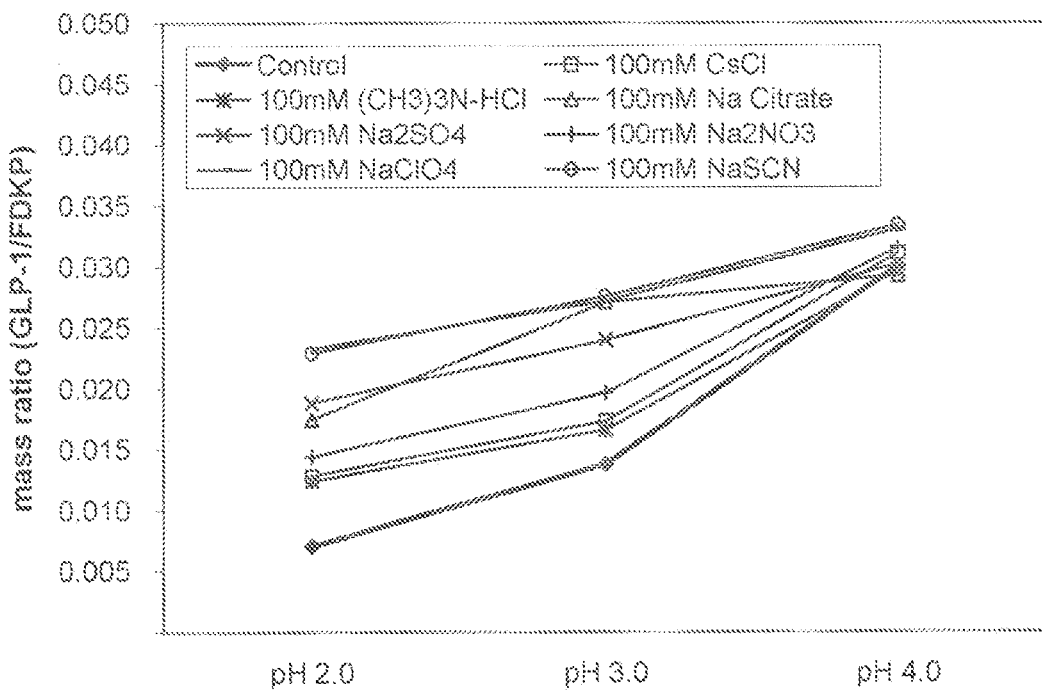
Figure 1C:
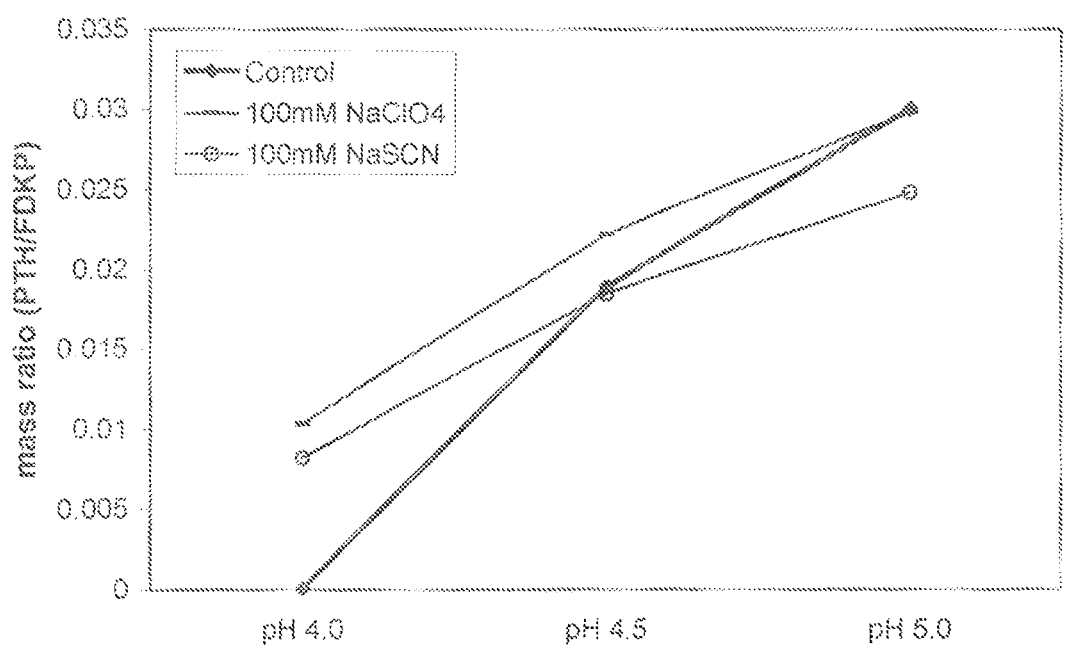

FIGS. 1A-1C depict the loading curves for insulin, GLP-1 and PTH respectively, onto the FDKP microparticle surface as a function of pH in the presence of the various chaotropes or kosmotropes. At low pH (3.0) all chaotropes and kosmotropes analyzed improved the affinity of insulin for the microparticle surface and showed significant loading compared to the control (FIG. 1A). At pH 4, this effect was not observed (FIG. 1A). At higher pH (5.0), the chaotropes and kosmotropes interfered with the adsorption of insulin to the microparticle surface, as compared to control, by precipitating the insulin protein. Thus these agents promoted binding of insulin to the FDKP particles at lower pH, but have little or even a detrimental effect at the higher pH conditions.

GLP-1, in the presence of chaotropes and kosmotropes, showed an improved affinity for the FDKP microparticles at pH 2.0-4.0 with a greater effect at lower pH (FIG. 1B). Similar observations were disclosed in U.S. Provisional Application Ser. No. 60/744,882. There it was noted, that approximately 0.02-0.04 mg/mL of the GLP-1 peptide (which corresponds to mass ratios of 0.004 to 0.008) was detected in the reconstituted microparticle-free control samples in the presence of NaSCN, $NaClO_4$, $Na_2SO_4$, $NaNO_3$ and Na citrate, indicating that a small proportion of the GLP-1 precipitated rather than adsorbing to the particle.

The affinity of PTH for the FDKP microparticle surface was greater at pH of 4.0 to about 4.5 in the presence of strong chaotropes NaSCN and $NaClO_4$ (FIG. 1C).

The data supports that chaotropic and kosmotropic agents play a role in promoting adsorption of the active agent to FDKP microparticle surfaces, most notably at low pH. Since these modifiers have a greater effect at low pH, where the microparticle surface is less ionic, it is likely that adsorption results from a hydrophobic mechanism. The decrease in adsorption observed at higher pH may result from the more highly charged surface of the particle in combination with effects chaotropic and kosmotropic agents have on increasing the hydrophobicity of the active agents. Additionally, as ionic species, these agents may compete with the active agent for binding to the microparticle, or disrupt the electrostatic interactions between the active agent and the microparticle. Finally it is also noted that Debye shielding can contribute to the decrease in adsorption to the more highly charged surface.

Example 3

Effect of Osmolytes on Adsorption of Active Agent to FDKP Particles

Figure 2A:
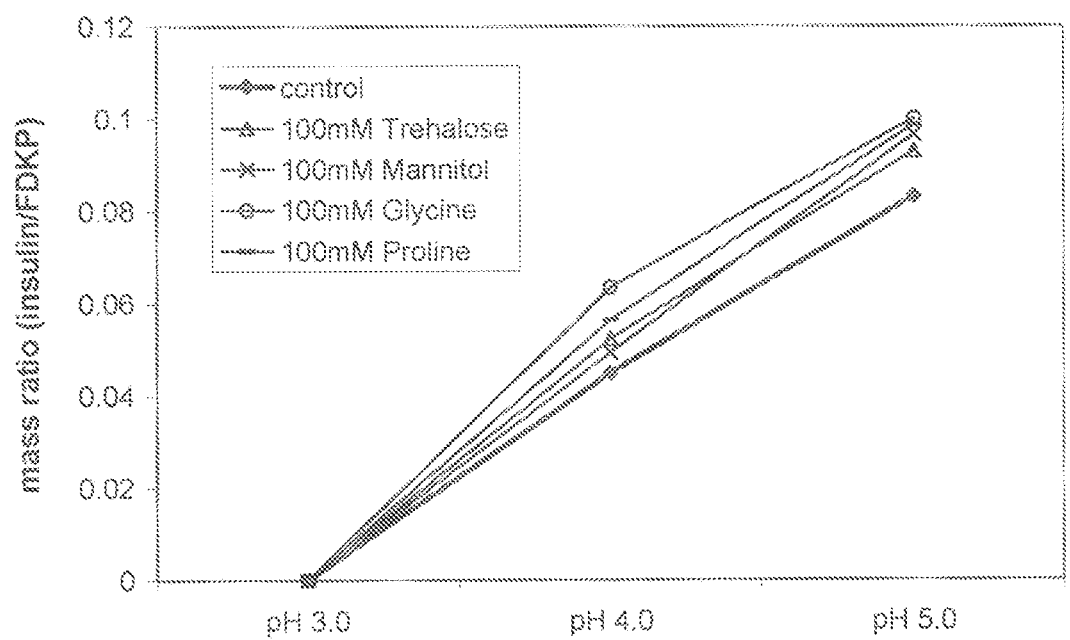
Figure 2B:
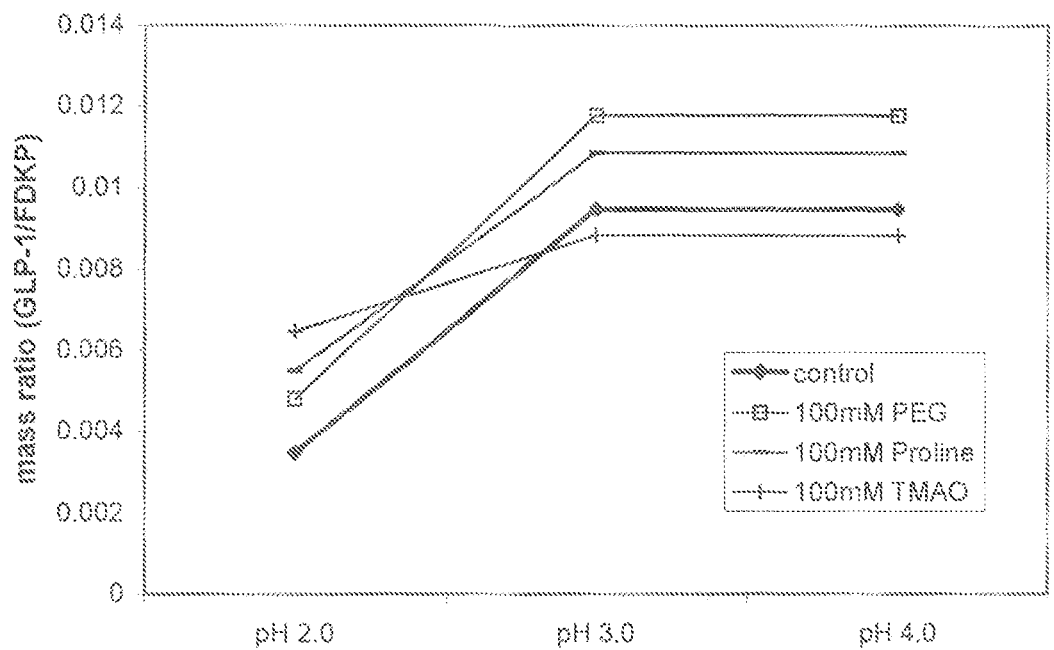
Figure 2C:
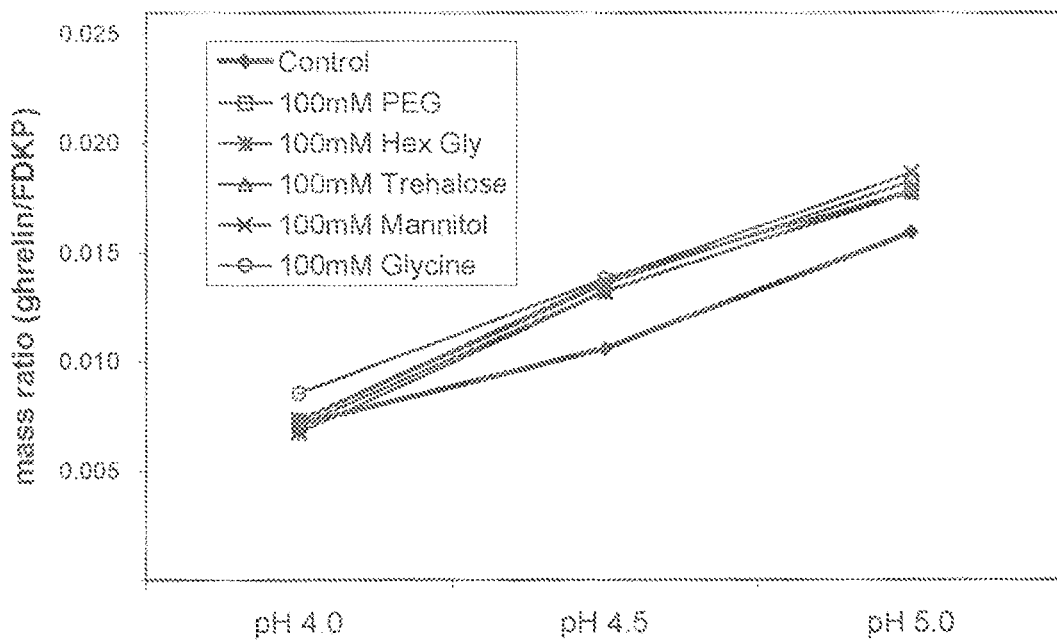

To assess the importance of active agent stability on adsorption, the effect of osmolytes on the binding of active agent to FDKP particles was examined by HPLC analysis. FIGS. 2A-2C show the loading curves for insulin (FIG. 2A), GLP-1 (FIG. 2B) and ghrelin (FIG. 2C) onto FDKP particles as a function of pH in the presence of common stabilizers (osmolytes). Loading of the active agent onto FDKP microparticles was performed at 5 mg/mL of microparticles and an insulin concentration of 0.75 mg/mL (15% w/w), or a GLP-1 concentration of 0.25 mg/mL (5% w/w) or a ghrelin concentration of 0.10 mg/mL (2% w/w). The concentration of the osmolyte (stabilizer) in the samples was held constant at 100 mM and the pH varied from about 2.0 to about 5.0. The osmolytes were selected from hexylene-glycol (Hex-Gly), trehalose, glycine, PEG, TMAO, mannitol and proline; the control indicates no osmolyte.

Of the active agents studied, insulin showed significantly improved affinity for the FDKP particle surface in the presence of osmolytes (PEG, glycine, trehalose, mannitol and Hex-Gly) over a pH range of 3.0 to 5.0 (FIG. 2A). Of the osmolytes studied, PEG and proline improved the affinity for adsorption of the GLP-1 onto FDKP particle surface over a pH range from 2.0 to 4.0. The osmolyte TMAO was more effective than PEG or proline at binding GLP-1 onto the FDKP microparticle surface at low pH (2.0) but was modestly detrimental at pH 3.0 and above (FIG. 2B). Ghrelin however, showed greater affinity for the microparticle surface in the presence of 100 mM mannitol, PEG, glycine, Hex-Gly, and trehalose when compared to the control over the pH range of about 4.0 to 5.0 (FIG. 2C).

These loading curves suggested that osmolytes are capable of enhancing the adsorption of the active agent to FDKP microparticle surface. It is likely that this effect resulted from the modifiers ability to stabilize the active agent, which enabled adsorption to be more energetically favorable.

Example 4

Effect of Alcohols on Affinity of Active Agent to FDKP Particles

In assessing the effect of modifiers on the active agent that allows for adsorption to the microparticle surface by a hydrophobic mechanism, the effect of alcohols were examined. Alcohols known to induce helical conformation in unstructured peptides and proteins by increasing hydrogen-bonding strength were evaluated to determine the role that helical confirmation plays in adsorption of active agent to FDKP particles surface. Active agents such as GLP-1 and ghrelin were analyzed. Loading of the active agent on FDKP particles was performed at 5 mg/mL of microparticles and a GLP-1 concentration of 0.25 mg/mL (5% w/w) or a ghrelin concentration of 0.10 mg/mL (2% w/w). The effect of each alcohol was observed over a pH range of 2.0 to 5.0. The alcohols used were trifluoroethanol (TFE) and hexafluoroisopropanol (HFIP). Each alcohol was evaluated at varying concentrations which include 5%, 10%, 15%, or 20% v/v.

Figure 3A:
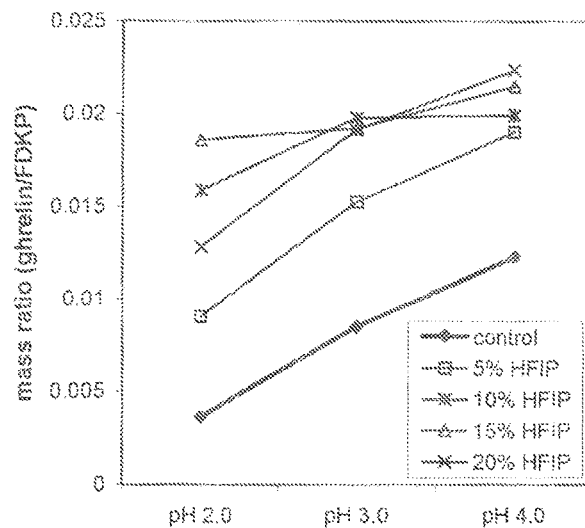
Figure 3B:
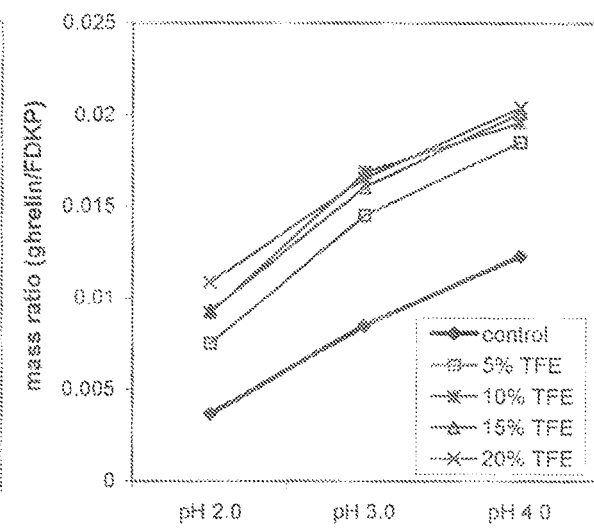

FIGS. 3A-3D show the loading curves for active agent onto FDKP microparticles as a function of pH for each alcohol and each active agent. At pH 2.0-4.0, ghrelin showed greatly improved affinity for the microparticle surface in the presence of HFIP and TFE at all concentrations tested (5%, 10%, 15% and 20%), as demonstrated by the mass ratio of ghrelin to FDKP particles (FIGS. 3A-3B).

Figure 3C:
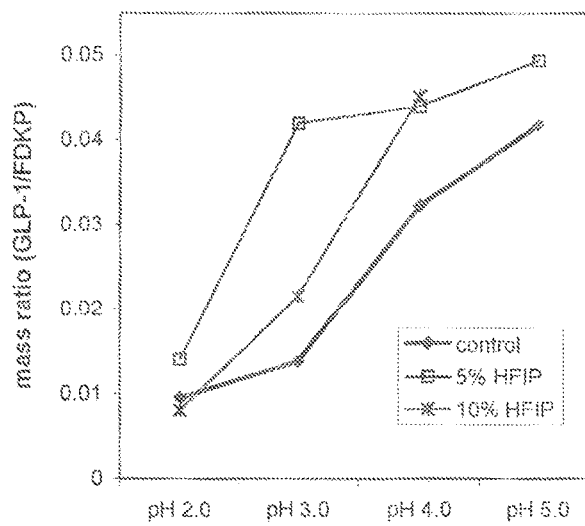
Figure 3D:
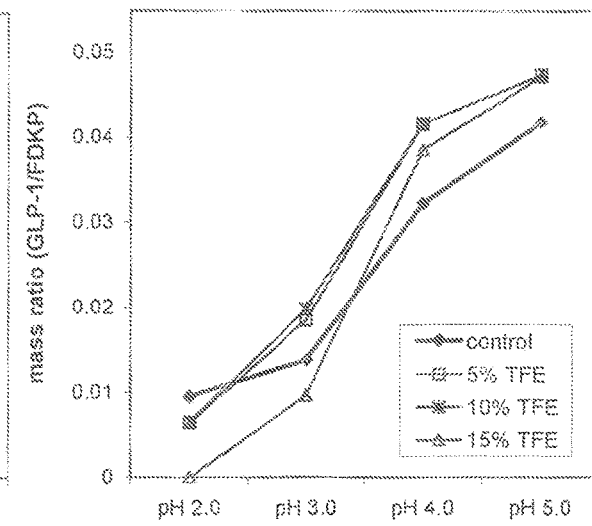

At pH 2.0-5.0, GLP-1 showed improved affinity for the microparticle surface in the presence of HFIP and TFE at the concentrations shown (5% and 10%) (FIGS. 3C-3D). The effect of TFE was less pronounced, and at the lower pHs tested was detrimental. It was noted that a substantial amount of GLP-1 peptide (0.13-0.19 mg/mL, which corresponds to mass ratios of 0.026 to 0.038) was detected in the reconstituted microparticle-free control samples in the presence of 10% HFIP and TFE at pH 4.0, indicating that some of the GLP-1 had precipitated. However, at lower pH (2.0-3.0), the amount of GLP-1 peptide detected in the reconstituted microparticle-free control in the presence of 10% HFIP or TFE was significantly decreased. At pH 3.0, GLP-1 peptide at 0 to 0.02 mg/mL, (which corresponding to a mass ratio of 0 to 0.004) was detected, whereas no GLP-1 was detected for the control samples at pH 2.0. The mass ratios in FIGS. 3C-D reflect both adsorbed and precipitated active agent although precipitation is an increasingly minor component as the pH decreased toward 3.0.

The data indicated that alcohols are able to improve the adsorption of the active agent onto FDKP microparticles. This increase in adsorption likely resulted from enhanced hydrophobic interactions between the active agent and surface of the microparticle in the presence of alcohols.

Example 5

Effect of Salt on Adsorption of Active Agent to FDKP Particles

To further address the hydrophobic mechanism of binding, the effects of salt on adsorption of active agent to FDKP microparticles were observed by HPLC analysis.

Figure 4A:
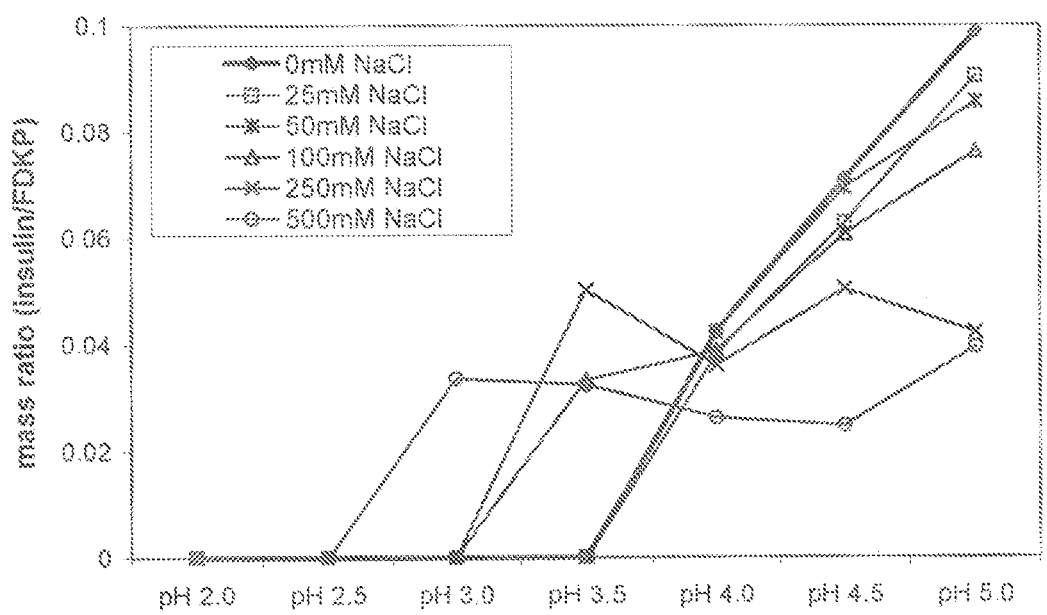
Figure 4B:
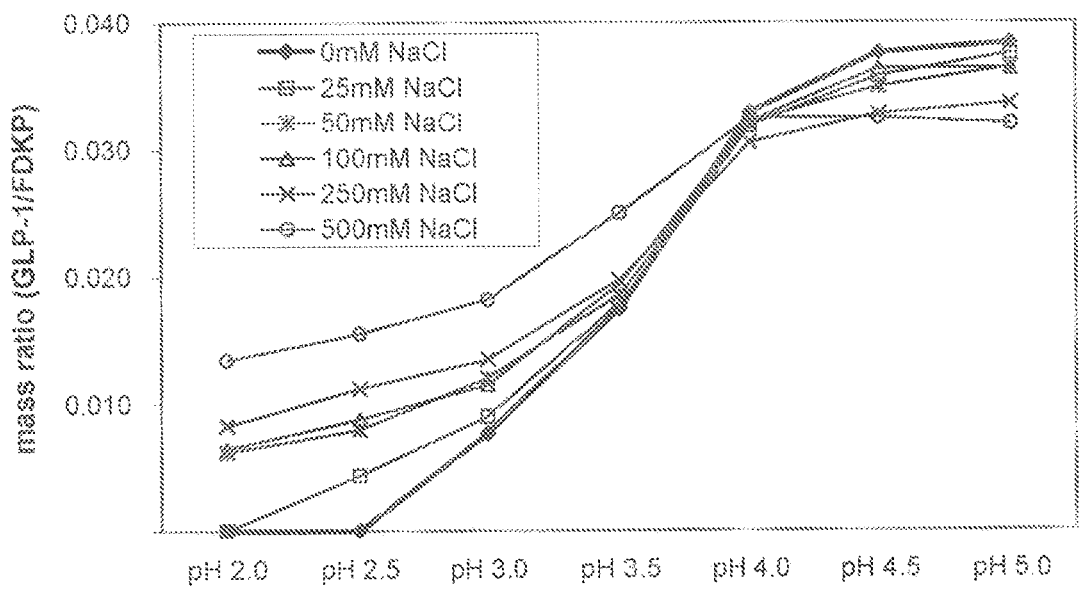

Loading of the active agent onto FDKP microparticles was performed at 5 mg/mL of microparticles and an insulin concentration of 0.75 mg/mL (15% w/w), or a GLP-1 concentration of 0.25 mg/mL (5% w/w) or a PTH concentration of 0.25 mg/mL (5% w/w) in the presence of 0, 25, 50, 100, 250, and 500 mM NaCl (FIGS. 4A-4C). Loading of PTH onto FDKP particles was also assessed at 1000 mM NaCl. The amount of active agent detected in reconstituted microparticle-free control samples as a function of pH and NaCl concentration was assessed. The pH was controlled with a 20 mM potassium phosphate/20 mM potassium acetate mixture.

As observed in FIG. 4A, increased binding (adsorption) of insulin onto FDKP particles was evident at high salt concentrations of 100-500 mM at pH from about 2.5 to about 3.5. At a pH from about 4.0 to about 5.0, for all salt concentrations tested, a reduction in the adsorption of insulin to the FDKP particle was observed.

At a pH from about 2.0 to about 3.5 enhanced binding (adsorption) of GLP-1 to FDKP particles was evident at all the salt concentrations tested (FIG. 4B). At pH 4.0 and above, a reduction in binding was also noted.

Similar studies using PTH as the active agent showed enhanced binding of PTH to the FDKP particles at high salt concentrations of 250 to 1000 mM at pH from about 2.0 to about 3.5 (FIG. 4C). At pH from about 3.5 to about 5.0 binding of PTH to the microparticle decreased in the presence of salt.

Figure 4D:
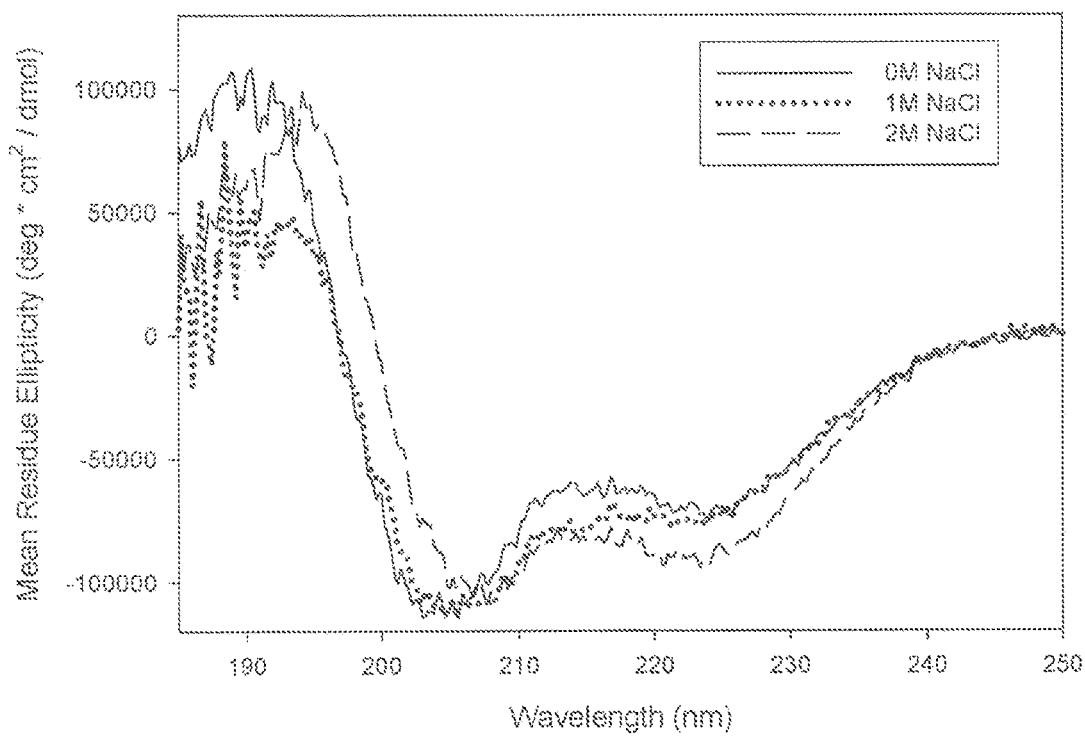

At low pH, where adsorption is not favorable, the addition of salt was able to modify the chemical potential of the active agent so as to increase its affinity for the microparticle surface. Such enhancement of binding likely resulted from a hydrophobic mechanism. Furthermore, the data indicated that as the pH was raised, adsorption decreased with increased salt concentration. As the microparticle surface became more charged with increasing pH, the hypothesized hydrophobic mechanism can be expected to be less effective at promoting the adsorption of the active agent. This reduction may also have resulted from salt competing for the binding sites on the surface of the microparticle. It is noted that Debye shielding may also contribute to the reduced adsorption observed The data also showed that salt is capable of altering the structure of active agents. For example, circular dichroism measurements with PTH showed that as the salt concentration increased the secondary structure of the peptide adopted a more helical conformation (FIG. 4D). This suggests that change in the structure of PTH may promote its binding to the microparticle surface at low pH.

In an aqueous solution, the presence of salt was also shown to partition the dye Texas Red onto the surface of the microparticle.

Example 6

Effects on Cyclosporin a Adsorption to FDKP Particles

The effects on the adsorption of small hydrophobic molecules onto FDKP particles was investigated both in vitro and in vivo using cyclosporin A as the active agent. Adsorption was promoted by altering the solubility of the active agent.

Cyclosporin A, a lipophilic cyclic polypeptide, was studied in order to show how a hydrophobic molecule can be made to adsorb to microparticles. In addition, the size of cyclosporin A (1202.61 MW) was utilized to demonstrate the loading capacities of microparticles for smaller compounds.

To accomplish loading, a solvent/anti-solvent method was employed. The basic principle of this methodology is to dissolve the compound in a solvent (methanol) and then use anti-solvent (water) to drive the compound out of solution and onto the surface of the microparticles. Utilizing this solvent/anti-solvent approach, cyclosporin A was successfully loaded onto the surface of microparticles.

In a preliminary experiment to determine a solubility profile, cyclosporin A was dissolved to 10 mg/mL in methanol and its solubility at 1 mg/mL with varying concentrations of anti-solvent (10-90% $H_2O$ in 10% increments) was analyzed by HPLC. The cyclosporin A peak areas were compared against the sample containing methanol alone, to determine the percent loss to precipitation. It was observed that solubility was largely retained below 60% $H_2O$. At 70% $H_2O$, a significant majority of the agent was insoluble and at 80-90% $H_2O$ less than 5% solubility remained.

Figure 5A:
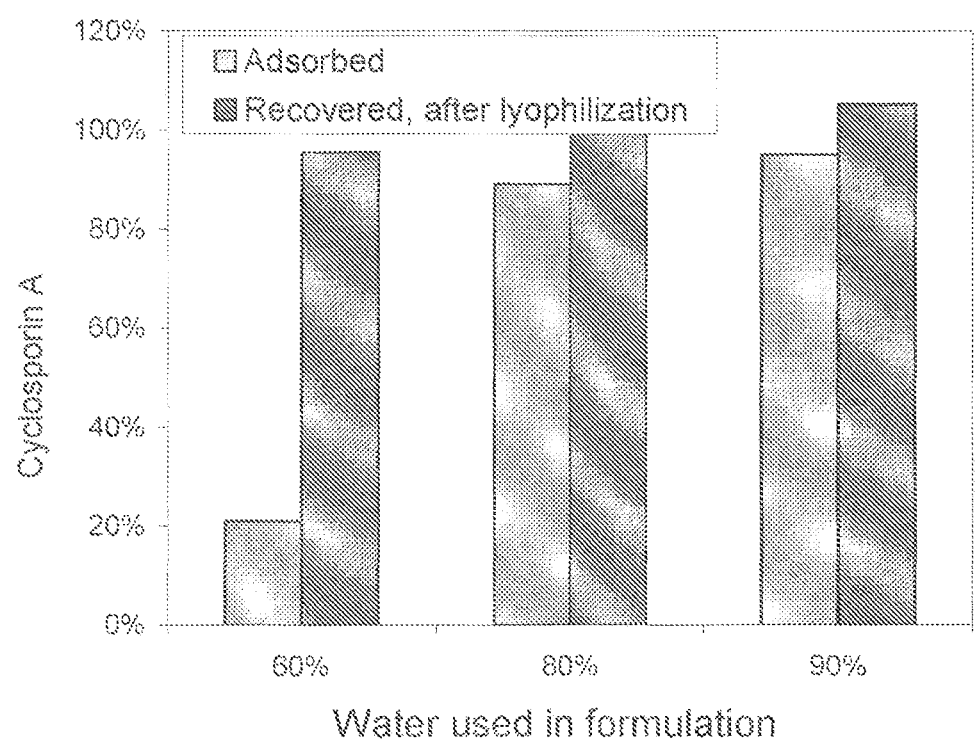

To assess particle loading, FDKP microparticles were suspended in methanol solutions of cyclosporin A. Water was then added in a stepwise fashion to final concentrations of 60, 80, and 90%. Half of the sample was pelleted and the other half lyophilized. Each half was then redissolved such that the final percentages were 20% FDKP microparticles/cyclosporin A, 20% 0.5 M ammonium bicarbonate (AmBicarb), and 60% methanol (the concentrations necessary for the dissolution of both microparticle and cyclosporin A). The cyclosporin A content of each was analyzed by HPLC and compared to determine the proportion that had become adsorbed to the particle. The results are presented in FIG. 5A. At 60% $H_2O$ it was observed that about 20% of the cyclosporin A had bound to the particle. At 80% and 90% $H_2O$ the loads were about 90% and 95%, respectively, indicating the strong binding of cyclosporin A to FDKP microparticles.

Figure 5B:
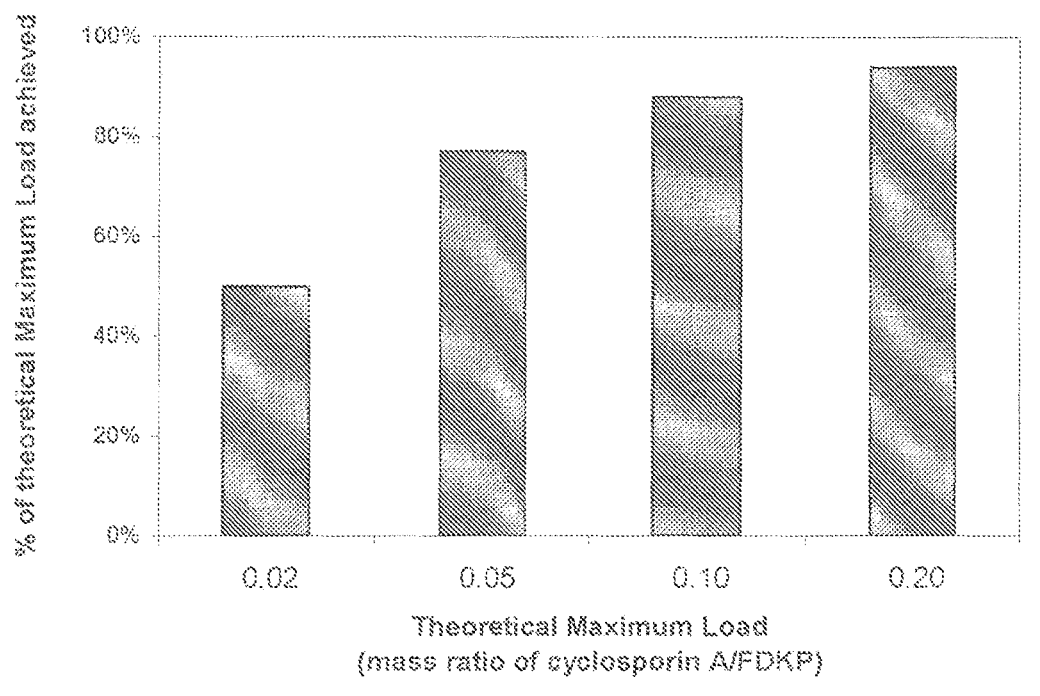

The loading capacity of the microparticles for cyclosporin A was analyzed at the 90% anti-solvent level by varying the input of cyclosporin A so that the final content of the recovered solids would be from 2% to 20%, assuming all of the cyclosporin A became adsorbed. It was observed that as the input increased over this range the percent of available cyclosporin A bound to the microparticle increased from 50% to 95% of the input (FIG. 5B). It is to be noted that, taking into account that the solubility of cyclosporin A is 0.05 mg/mL at 90% $H_2O$, these results indicated that substantially all of the insoluble cyclosporin A became adsorbed to the particles rather than precipitating out.

Example 7

Pulmonary Insufflation of Cyclosporin A/DKP Particles

To examine the pharmacokinetics of cyclosporin A/FDKP microparticles, plasma concentrations of cyclosporin A were evaluated in female Sprague Dawley rats administered various formulations of cyclosporin A/FDKP microparticles via pulmonary insufflation or intravenous injection. These studies were conducted using cyclosporin A/FDKP microparticles made at 90% anti-solvent and a theoretical maximum mass ratio of 0.05, 0.10 or 0.20 as described in the example above. These are referred to as the 5%, 10% and 20% loads.

A single dose of 2.5 mg cyclosporin A/FDKP microparticles was delivered to eight groups of rats via pulmonary insufflation or intravenous injection. Blood samples were taken on the day of dosing for each group at pre-dose (time 0), and at 5, 20, 40, 60, 240, 480 minutes and at 24 hrs post dose. At each time point, approximately 100 ℮L whole blood was collected from the lateral tail vein into a cryovial, inverted and stored on ice. Blood samples were centrifuged at 4000 rpm and approximately 40 ℮L plasma was pipetted into 96-well plates which were stored at −80° C. until analyzed.

Figure 6:
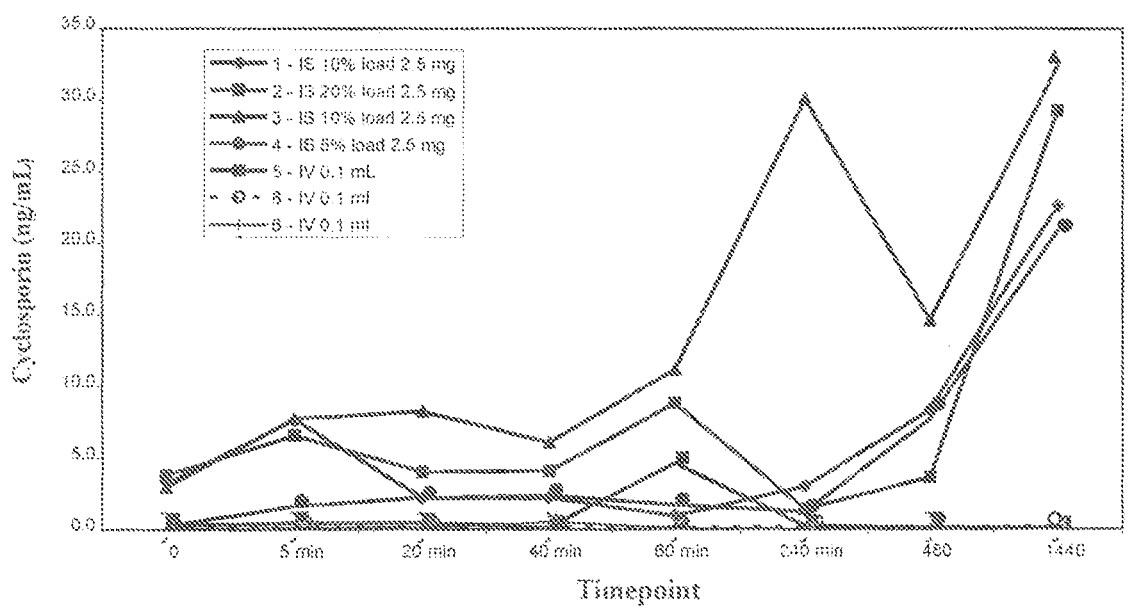

As shown in FIG. 6, administration of 2.5 mg FDKP microparticles/cyclosporin A via pulmonary insufflation resulted in maximal serum cyclosporin levels 24 hours post dose in female Sprague Dawley rats. The 10% load achieved a Cmax of 32.4 ng/mL at that time point. Animals administered 2.5 mg of FDKP microparticles/cyclosporin A in 0.1 mL via intravenous injection showed minimal levels of cyclosporin out to 24 hours post dose. It was observed that FDKP microparticle levels peaked at 20 minutes post dose and returned to baseline levels in 4 hours for both the intravenous and pulmonary insufflation groups.

Overall, the data shows the bioavailability of cyclosporin A/FDKP microparticle. It is noted that the single peak at 240 minutes is an anomaly. For all animals treated, the pathology as determined by gross and microscopic observation was normal.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A method for making a microparticle coated with an active agent that is of pharmaceutical use, the method comprising:
   (i) obtaining a crystalline fumaryl diketopiperazine microparticle wherein the crystalline diketopiperazine microparticle does not comprise an active agent;
   (ii) forming a suspension comprising said crystalline diketopiperazine microparticle and a solvent;
   (iii) dissolving said active agent in the fluid phase of said suspension;
   (iv) increasing the pH of the fluid phase to about 4 to 5;
   (v) adsorbing of said active agent onto a surface of said crystalline fumaryl diketopiperazine microparticle to provide a coating of said active agent on said crystalline fumaryl diketopiperazine microparticle; and
   (vi) removing or exchanging said solvent after step (v).

2. The method of claim 1, wherein the active agent is a protein, peptide, or polypeptide.

3. The method of claim 1, wherein the active agent is glucagon-like peptide 1 (GLP-1).

4. The method of claim 1, wherein the active agent is vasoactive.

5. The method of claim 1, wherein the active agent is a neuroactive agent.

6. The method of claim 1, wherein the active agent is a hormone.

7. The method of claim 1, wherein the active agent is an anticoagulant.

8. The method of claim 1, wherein the active agent is an immunomodulating agent.

9. The method of claim 1, wherein the active agent is a cytotoxic agent.

10. The method of claim 1, wherein the active agent is an antibiotic agent.

11. The method of claim 1, wherein the active agent is an antiviral agent.

12. The method of claim 1, wherein the active agent is an antigenic agent.

13. The method of claim 1, wherein the active agent is an antibody.

14. The method of claim 1, wherein the active agent is a small molecule.

15. The method of claim 1, wherein the active agent is a nucleic acid molecule.

* * * * *